United States Patent [19]

Hosoda

[11] 4,429,686
[45] Feb. 7, 1984

[54] ENDOSCOPE LIGHT SUPPLY DEVICE
[75] Inventor: Seiichi Hosoda, Fuchu, Japan
[73] Assignee: Olympus Optical Co., Ltd., Tokyo, Japan
[21] Appl. No.: 415,459
[22] Filed: Sep. 7, 1982

Related U.S. Application Data

[63] Continuation of Ser. No. 214,096, Dec. 8, 1980, abandoned.

[30] Foreign Application Priority Data

Dec. 20, 1979 [JP] Japan .................................. 54-166195

[51] Int. Cl.³ ............................................. A61B 1/06
[52] U.S. Cl. ........................................................ 128/6
[58] Field of Search ....................................... 128/4–8; 354/62

[56] References Cited

U.S. PATENT DOCUMENTS 3,599,630  8/1971  Sato et al. .............................. 128/6
4,053,756 10/1977  Takahashi .............................. 128/6

Primary Examiner—Kyle L. Howell
Assistant Examiner—Max F. Hindenburg
Attorney, Agent, or Firm—Frishauf, Holtz, Goodman and Woodward

[57] ABSTRACT

A change-over is carried out from an observation light path to a photographing light path in response to a synchronizing signal. After the observation light source is extinguished, the photographing light source flashes a light.

2 Claims, 6 Drawing Figures

ENDOSCOPE LIGHT SUPPLY DEVICE

This is a continuation of application Ser. No. 214,096 filed Dec. 8, 1980, now abandoned.

BACKGROUND OF THE INVENTION

This invention relates to an endoscope light supply device, and more particularly to a 2-lamp type light supply device comprising an observation light source and photographic light source.

With the conventional 2-lamp type light supply device comprising an observation light source or an incandescent lamp and a photographing light source or an electronic flash tubes, an observation light path and photographing light path are changed over to each other by shifting the position of a mirror. At this time, an observation light is shut off by changing the mirror position, before a camera shutter is opened. After the camera shutter is opened, a film frame is exposed to an image illuminated by a photographing light. When, however, a film frame is going to be exposed to the illuminated image, remnant reflections of an observation light from the surrounding parts of the mirror are undesirably carried into a light guide, giving rise to the so-called fogging on an exposed film. Generally, it will well serve the purpose of photographing if a film frame is exposed to an electronic flash light only for an instant. In this case, however, remnant reflections of an observation light from the surrounding parts of the mirror subject the film frame to overexposure. Intrusion of an observation light derived from tungsten changes the color purity of a photograph obtained by exposing a film to a white strobe light.

It is accordingly the object of this invention to provide an endoscope light supply device which ensures a good endoscope photograph without being affected by an observation light.

SUMMARY OF THE INVENTION

To attain the above-mentioned object, this invention provides an endoscope light supply device, wherein an observation light path is changed over to a photographing light path in response to a synchronizing signal and an observation light source is extinguished, and wherein when a camera shutter is opened, a photographing light source is actuated to take a photograph.

DETAILED DESCRIPTION

Figure 1:
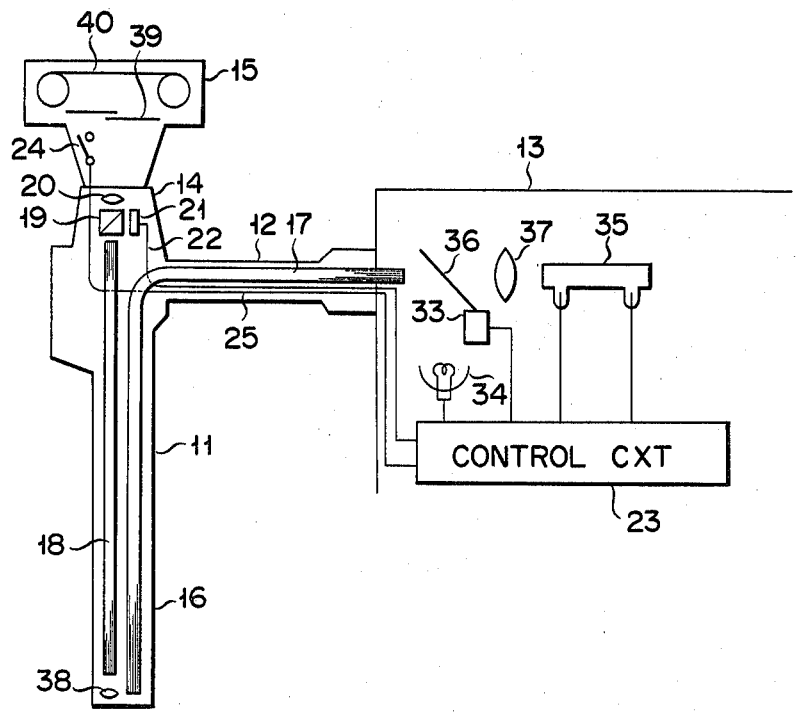
FIG. 1 shows the arrangement of an endoscope system including an endoscope light supply device according to one embodiment of this invention.

Referring to FIG. 1, a connector section 12 of an endoscope 11 is connected to a light source unit 13. An eyepiece section 14 is fitted with a photographic camera 15. The endoscope comprises a light guide 17 extending from the distal end of an insertion section 16 through the connector 12 to the light source unit 13 and an image guide 18 extending from the distal end of the insertion section 16 to the eyepiece section 14. The eyepiece section 14 is fitted with a beam splitter 19 and an eyepiece lens 20. A light-receiving element (e.g. photodiode) 21 facing the beam splitter 19 is connected to a control circuit 23 of the light source unit 13 through a lead 22. A synchronizing contact 24 provided in a photographic camera 15 is connected to the control circuit 23 of the light source unit 13 through a lead 25 extending through the endoscope 11.

Figure 2:
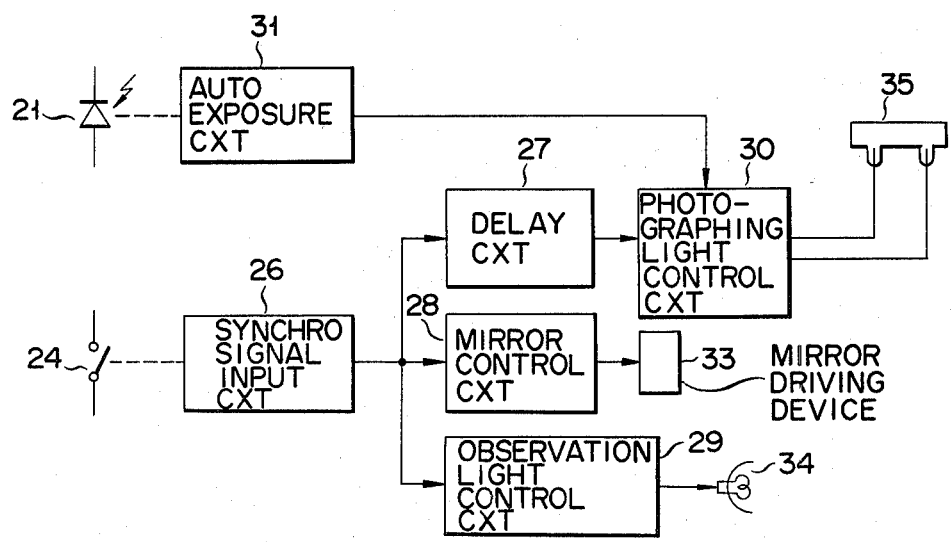
FIG. 2 indicates the arrangement of a control circuit used with the endoscope light supply device of FIG. 1.

As shown in FIG. 2, the control circuit 23 comprises a synchronizing signal input circuit 26 connected to a synchronizing contact 24. The output terminal of the synchronizing signal input circuit 26 is connected to a delay circuit 27, mirror control circuit 28 and observation light control circuit 29. The output terminal of the delay circuit 27 is connected to a photographing light control circuit 30. This photographing light control circuit 30 is connected to an autoexposure circuit 31 for defining an exposure value in accordance with a photocurrent signal emitted from the light-receiving element 21. Output signals from the mirror control circuit 28, observation light control circuit 29 and photographing light control circuit 30 respectively control the operation of a mirror-driving device 33, observation light source or incandescent lamp 34 and photographing light source or electronic flash tube 35 all included in the light source unit 13 of FIG. 1. The mirror control circuit 28 formed of, for example, an RS flip-flop circuit, actuates the mirror-driving device 33 in response to a synchronizing signal. The photographing light control circuit 30 is so arranged as to cause an electronic flash tube 35 to flash a light in response to an output signal from the delay circuit 27, and prevent the electronic flash tube 35 from flashing a light in response to an output signal from the autoexposure circuit 31. The photographing light control circuit 30 is formed of the ordinary electronic flash light control circuit comprising a flash-starting trigger circuit and flash-stopping trigger circuit. The autoexposure circuit 31 is also formed of the ordinary light-measuring circuit including, for example, an integration circuit and comparator.

Figure 3:
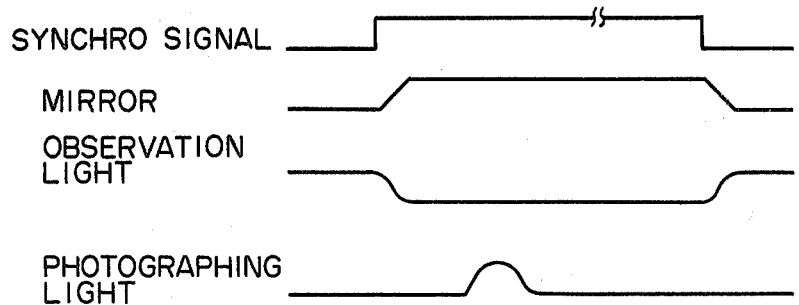
FIG. 3 is a time chart illustrating the operation of the endoscope system of FIG. 1.

When, with an endoscope light supply device arranged as described above, a release button (not shown) of the photographic camera is depressed, the synchronizing contact 24 is actuated, causing the synchronizing signal input circuit 26 to send forth a synchronizing signal illustrated in FIG. 3. The delay circuit 27, mirror control circuit 28 and observation light control circuit 29 are put into operation in response to the synchronizing signal. As a result, the mirror-driving device 33 is actuated to remove the mirror 36 from the light path of the electronic flash tube 35 and extinguish the observation light source 34. This condition is indicated in the time chart of FIG. 3. When the position of the mirror 36 has been fully changed and the observation light source 34 has been completely extinguished, then the shutter 39 of the photographic camera 15 is opened. At this time, the photographing light control circuit 30 is actuated in response to an output signal from the delay circuit 27, causing the electronic flash tube 35 to flash a light. A light flashing by the electronic flash tube 35 is conducted through a lens 37 to the light input terminal of the light guide 17 extending through the endoscope 11.

When an electronic flash light conducted through the light guide 17 illuminates a foreground subject, then reflections from the foreground subject are shed on a film frame 40 after passing through an object lens 38, image guide 18, beam splitter 19, eyepiece lens 20 and shutter 39. Part of reflections diverted by the beam splitter 19 are supplied to the light-receiving element 21, which in turn generates a photocurrent signal corresponding to an amount of a light received. The autoexposure circuit 31 measures the amount of light shed on a film frame in accordance with the photocurrent signal emitted from the light-receiving element 21. When measuring a proper amount of an irradiated light, the autoexposure circuit 31 sends an illumination stop signal to the photographing light control circuit 30. The electronic flash tube 35 ceases to flash a light in response to the illumination stop signal.

With an endoscope light supply device embodying this invention, a camera shutter is opened, as described above, when the position of the mirror has been fully shifted and an observation light has been completely extinguished. Later, the electronic flash tube 35 flashes a light. At the time of photographing, therefore, remnant reflections of the observation light are not shed on a film frame at all, ensuring good photographing with proper exposure and good color purity. When the camera shutter is closed at a prescribed shutter speed, after the electronic flash light photographing is brought to an end, then the mirror 36 regains its original position, and the observation light source sends forth a light again.

Figure 4:
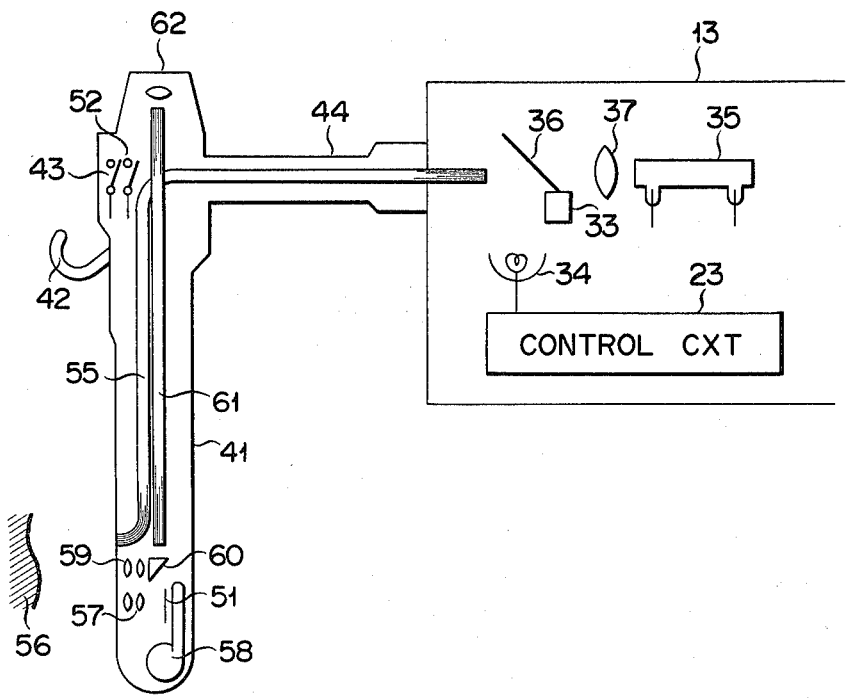
FIG. 4 indicates the arrangement of an endoscope system including an endoscope light supply device according to another embodiment of the invention.
Figure 5:
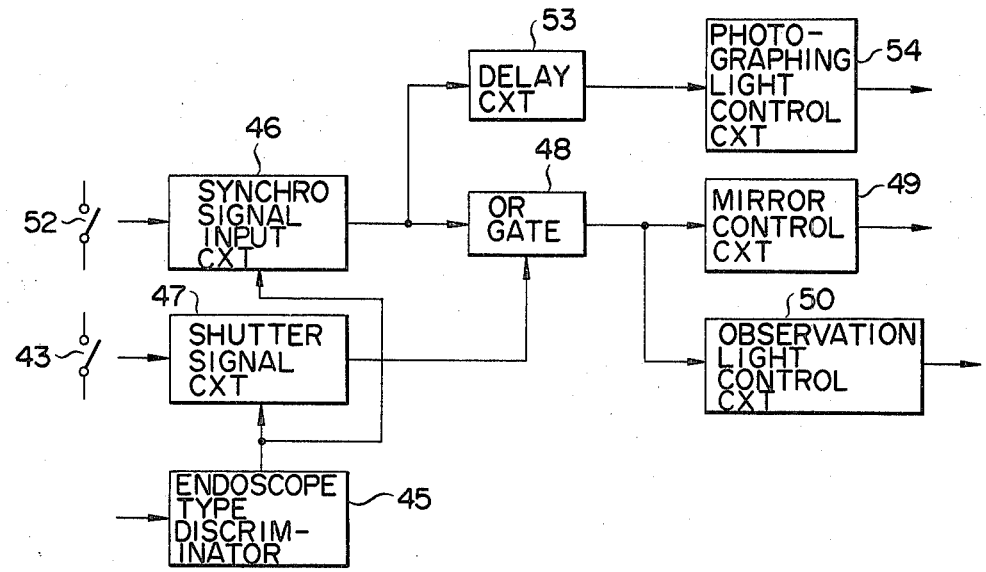
FIG. 5 shows the arrangement of a control circuit used with the endoscope light supply device of FIG. 4.
Figure 6:
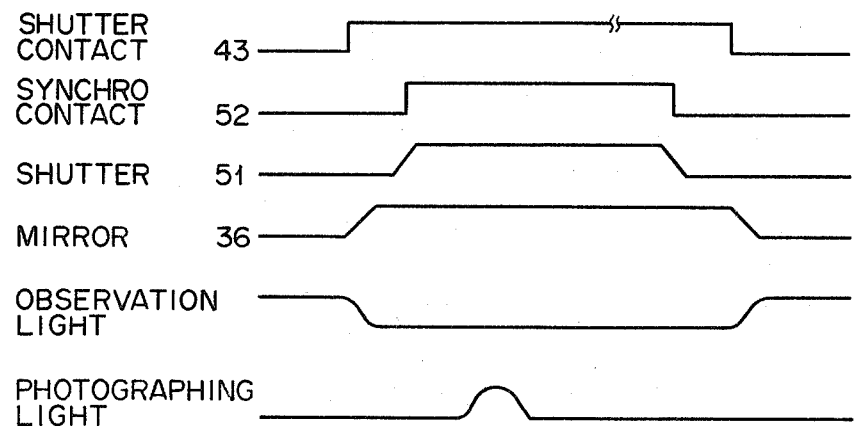
FIG. 6 is a time chart illustrating the operation of the endoscope system of FIGS. 4 and 5.

Description is now given with reference to FIGS. 4 and 5 of an endoscope light supply device according to another embodiment of this invention. With this embodiment, a endoscope 41 comprises an photographic camera built in the distal end portion. When a photographing lever 42 is operated, a shutter is released. When the lever 42 is brought back to the original position, then an exposed film frame is taken up on a reel. When a connector 44 of the above-mentioned endoscope 41 whose distal end portion is fitted with a photographic camera is connected to the light source unit 13, then an endoscope type discriminator 45 of the control circuit 23 judges that an endoscope in question is the type whose distal end portion is provided with a photographic camera, and sends forth an output signal denoting the result of the judgment to a synchronizing signal input circuit 46 and a shutter switch signal input circuit 47. When, under this condition, the photographing lever 42 is actuated, then the shutter contact 43 is closed, and the shutter switch signal input circuit 47 is operated to supply an output signal to an OR circuit 48. A signal conducted through the OR circuit 48 actuates a mirror control circuit 49 and observation light control circuit 50. As a result, the mirror 36 is removed from the light path of the electronic flash tube 35, and the observation light source 34 is extinguished. When the photographing lever 42 is further operated, then a shutter 51 is opened, and a synchronizing contact 52 is closed. The synchronizing signal input circuit 46 supplies an output signal to an OR circuit 48 and delay circuit 53 when the synchronizing contact 52 is closed. Where the delay circuit 53 actuates a photographing light control circuit 54 after a prescribed length of time, then the electronic flash tube 35 flashes a light. This light is shed on a foreground subject 56 through a light guide 55. Reflections from the foreground subject 56 are conducted through an object lens system of a photographic camera and shutter 51 to be shed on a film wound about a film cartridge 58. When the photographing lever 42 is brought back to its original position after photographing is brought to an end, then the synchronizing contact 52 and shutter contact 43 are opened. At this time, the mirror 36 regains its original position, and the observation light source 34 again sends forth a light. The exposed frames of a film are taken up on a reel. The above-mentioned operation cycle is carried out in a timing illustrated in a time chart of FIG. 6.

With the embodiment of FIGS. 4 and 5, the shutter contact 43 and synchronizing contact 52 are provided. The reason for this is that since a photographic camera is set in a limited space at the distal end of an endoscope, a shutter cannot be operated at a high speed; and consequently the observation light source 34 has to be extinguished before the opening of the shutter in order to suppress the emission of unnecessary light beams to a light guide 55. With the second embodiment of FIGS. 4 and 5, therefore, remnant reflections of an observation light from the surrounding parts of a photographic camera do not enter the light guide 55, ensuring proper photographing with good exposure and color purity.

At the time of observation, a light issued from the observation light source 34 is brought into the light guide 55 by means of the mirror 36. Reflections from a foreground subject are carried into an image guide 61 through a lens system 59 and prism 60. A light thus introduced is observed through an eyepiece section 62.

What is claimed is:

1. In an endoscope system including an endoscope light supply device to which is connected a connector of an endoscope, the endoscope including a light guide having an optical axis and an eyepiece section on which is mounted a photographing device having a releasable shutter, the light supply device comprising:

a signal source coupled to said photographing device for supplying a synchronizing signal in response to a shutter release operation of the photographing device during a photographing operation;

an electronic flash tube disposed on said optical axis of said light guide of said endoscope and selectively energizable during a photographing operation for irradiating a photographing light;

an incandescent lamp disposed on a light path substantially perpendicular to said optical axis of said light guide and emitting an observation light along said light path during an observation operation, said light path of said incandescent lamp crossing said optical axis of said light guide substantially perpendicularly at a crossing position;

a movable mirror arranged at said crossing position of said optical axis of said light guide and said light path of said incandescent lamp during an observation operation for reflecting said observation light from said incandescent lamp to said light guide along said optical axis of said light guide, said electronic flash tube being extinguished during said observation operation;

mirror driving means coupled to said signal source and to said movable mirror for moving said movable mirror away from said crossing position in response to said synchronizing signal during a photographing operation, thereby no longer reflecting observation light to said light guide and permitting only said photographing light from said electronic flash tube to be received at the light guide during a photographing operation; and means coupled to said signal source and to said incandescent lamp for extinguishing said incandescent lamp in response to said synchronizing signal during a photographing operation.

2. The endoscope light supply device of claim 1, further comprising a delay circuit coupled to said signal source and being operable in response to said synchronizing signal to produce a delayed output signal; and wherein said electronic flash tube is coupled to said delay circuit and irradiates said photographing light in response to said delayed output signal from said delay circuit.

* * * * *